United States Patent [19]

Rencavage

[11] Patent Number: 5,402,107
[45] Date of Patent: Mar. 28, 1995

[54] APPARATUS FOR SENSING BODY ATTITUDE

[75] Inventor: Michael A. Rencavage, Gouldsboro, Pa.

[73] Assignee: Allied Services Foundation, Inc., Scranton, Pa.

[21] Appl. No.: 11,336

[22] Filed: Jan. 29, 1993

[51] Int. Cl.6 .............................................. G08B 23/00
[52] U.S. Cl. .................................. 340/573; 128/782; 377/24.2
[58] Field of Search ................. 340/573, 689, 323 R; 128/782; 482/8; 377/24.2; 33/366

[56] References Cited

U.S. PATENT DOCUMENTS

| | | | |
|---|---|---|---|
| 3,670,320 | 6/1972 | Palmer | 340/573 |
| 4,112,926 | 9/1978 | Schulman et al. | 340/573 X |
| 4,191,949 | 3/1980 | Myers | 340/573 |
| 4,224,952 | 9/1980 | Sidorenko et al. | 128/782 |
| 4,503,622 | 3/1985 | Swartz et al. | 33/366 |
| 4,516,329 | 5/1985 | Dilcox | 340/689 X |
| 4,665,388 | 5/1987 | Ivie et al. | 340/573 |
| 4,871,998 | 10/1989 | Chaillou | 340/573 |
| 4,914,423 | 4/1990 | Fernandez | 340/573 |
| 4,938,476 | 7/1990 | Brunelle et al. | 340/573 X |
| 4,958,145 | 9/1990 | Morris | 340/689 |
| 5,089,808 | 2/1992 | Amirdash | 340/573 |
| 5,220,308 | 6/1993 | Batzdorff et al. | 340/573 |
| 5,300,921 | 4/1994 | Hoch et al. | 340/573 |

FOREIGN PATENT DOCUMENTS 2192475  1/1988  United Kingdom ............... 377/24.2

Primary Examiner—John K. Peng
Assistant Examiner—Thomas J. Mullen, Jr.
Attorney, Agent, or Firm—William H. Murray; Steve Mendelsohn; R. Anthony Diehl

[57] ABSTRACT

The apparatus is attached to a body part (for example, the back) of the user. The apparatus detects when the body part attitude exceeds a specific attitude range. For every such attitude violation, the apparatus sounds a buzzer and increments a displayed counter value that indicates the total number of such attitude violations. The apparatus may be used as part of physical therapy to modify the behavior of the user during routine physical activities. The sensitivity of the apparatus may be adjusted by controlling the specific attitude range.

11 Claims, 4 Drawing Sheets

APPARATUS FOR SENSING BODY ATTITUDE

BACKGROUND OF THE INVENTION

Field of the Invention

The present invention relates to the field of body attitude sensors, and, in particular, to the field of sensors, worn on a part of the body, that notify the user of when and how often the attitude of the body part deviates from a specific range of acceptable attitudes.

Statement of Related Art

After having back surgery or suffering some other back trauma, a patient may undergo physical therapy as part of his or her treatment. An important function of this therapy often is to assist the patient in altering his or her pattern of behavior during normal physical activity. In particular, it is often advantageous for the patient to maintain good posture during work and other activities of daily living.

It is known to use a back position attitude indicator device, such as those disclosed in U.S. Pat. No. 4,938,476 (Brunelle et al.) and U.S. Pat. No. 5,089,808 (Amirdash), to prevent back injuries during certain physical activities, such as lifting heavy objects. However, these devices are not designed to assist a physical therapist in providing and monitoring long-term treatment of a patient who has already suffered a back injury.

SUMMARY OF THE INVENTION

In a preferred embodiment, the present invention is an apparatus for sensing the attitude of a body part of a user. The apparatus comprises sensing means for generating a first signal when the attitude of the body part exceeds a specific attitude range. The apparatus further comprises counting means for receiving the first signal and for incrementing a counter value in accordance with the first signal.

In another preferred embodiment, the present invention is an apparatus for sensing the attitude of a body part of a user. The apparatus comprises a sensor module and a controller module. The sensor module comprises sensing means, a movable portion, and a fixed portion. The sensing means generates a first signal when the attitude of the body part exceeds a specific attitude range. The movable portion houses the sensing means. The fixed portion may be releasably secured to the body part and the movable portion may be releasably coupled to the fixed portion at two or more orientations to adjust the attitude range. The controller module comprises a power supply for providing electrical power to the sensor module and the controller module, and counting means for receiving the first signal and for incrementing a counter value in accordance with the first signal. The apparatus further comprises means for electrically connecting the sensor module to the controller module to transfer power from the power supply to the sensing means and to transmit the first signal from the sensing means to the counting means.

DETAILED DESCRIPTION OF THE INVENTION

In a preferred embodiment, the present invention is an apparatus for sensing the attitude of a body part of a user, the apparatus comprising sensing means for generating a first signal when the attitude of the body part exceeds a specific attitude range and counting means for receiving the first signal and for incrementing a counter in accordance with the first signal.

For example, when the apparatus is strapped to the user's torso, the apparatus may be used to count the number of attitude violations (i.e., the number of times the attitude of the user's back exceeds the specific attitude range). By logging the rate of attitude violations (e.g., number of violations per day or per specific type of activity), the long-term progress of the user in controlling his or her pattern of behavior of physical activity may be monitored.

Figure 1:
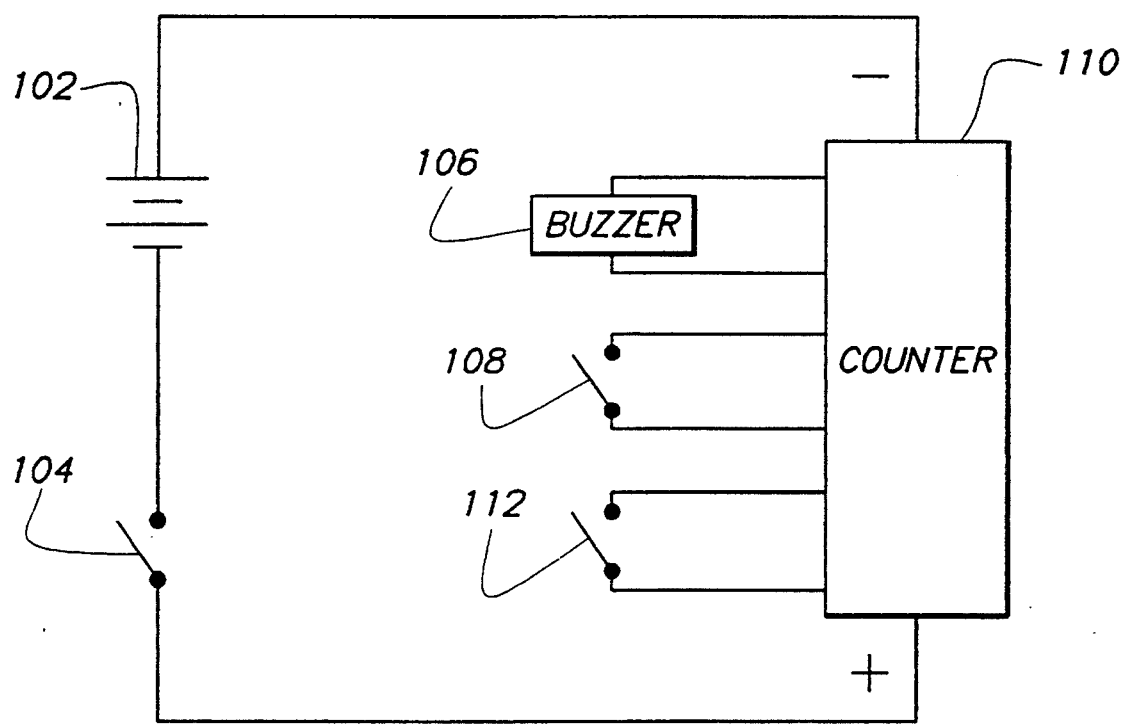
FIG. 1 is a schematic diagram of a body attitude sensing apparatus according to a preferred embodiment of the present invention.

Referring now to FIG. 1, there is shown a schematic diagram of body attitude sensing apparatus 100 according to a preferred embodiment of the present invention. Apparatus 100 may be secured to a user's torso or other body part or article of clothing by any suitable means, such as a belt 213, strap (not shown), or clip (not shown).

Battery 102 provides power to apparatus 100, which is turned on and off by power switch 104. When power switch 104 is closed, apparatus 100 is turned on. With apparatus 100 turned on, electronic buzzer 106 is activated to emit an audible tone when mercury switch 108 is closed. For every one time that mercury switch 108 closes and opens, electronic counting device 110 increments a counter value by one. Device 110 comprises a decimal-digit display (not shown) that continuously displays the current counter value. Every time reset switch 112 is closed, device 110 resets the counter value to zero.

In a preferred embodiment, apparatus 100 comprises two separate modules—a sensor module (not shown) and a controller module (not shown)—electrically connected by a flexible, expandable cable (not shown). The sensor module comprises the mercury switch 108, while the controller module comprises the other components of apparatus 100 depicted in FIG. 1.

With the sensor module secured to a user's torso, apparatus 100 can be used to determine when and how often the attitude of the user's back exceeds a specific attitude range. Every time such an attitude violation occurs, mercury switch 108 is closed and buzzer 106 sounds an alarm. When the user's back returns to within the specific attitude range, mercury switch 108 is opened, the alarm of buzzer 106 stops, and counting device 110 increments the displayed counter value by one.

As described in greater detail later in this specification in conjunction with FIG. 2, the sensor module can be adjusted to control the selection of the specific attitude range to make apparatus 100 more or less sensitive to deviations in the attitude of the user's back. This sensitivity control may be used to accommodate different patients as well as different physical tasks by the same patient.

Figure 2:
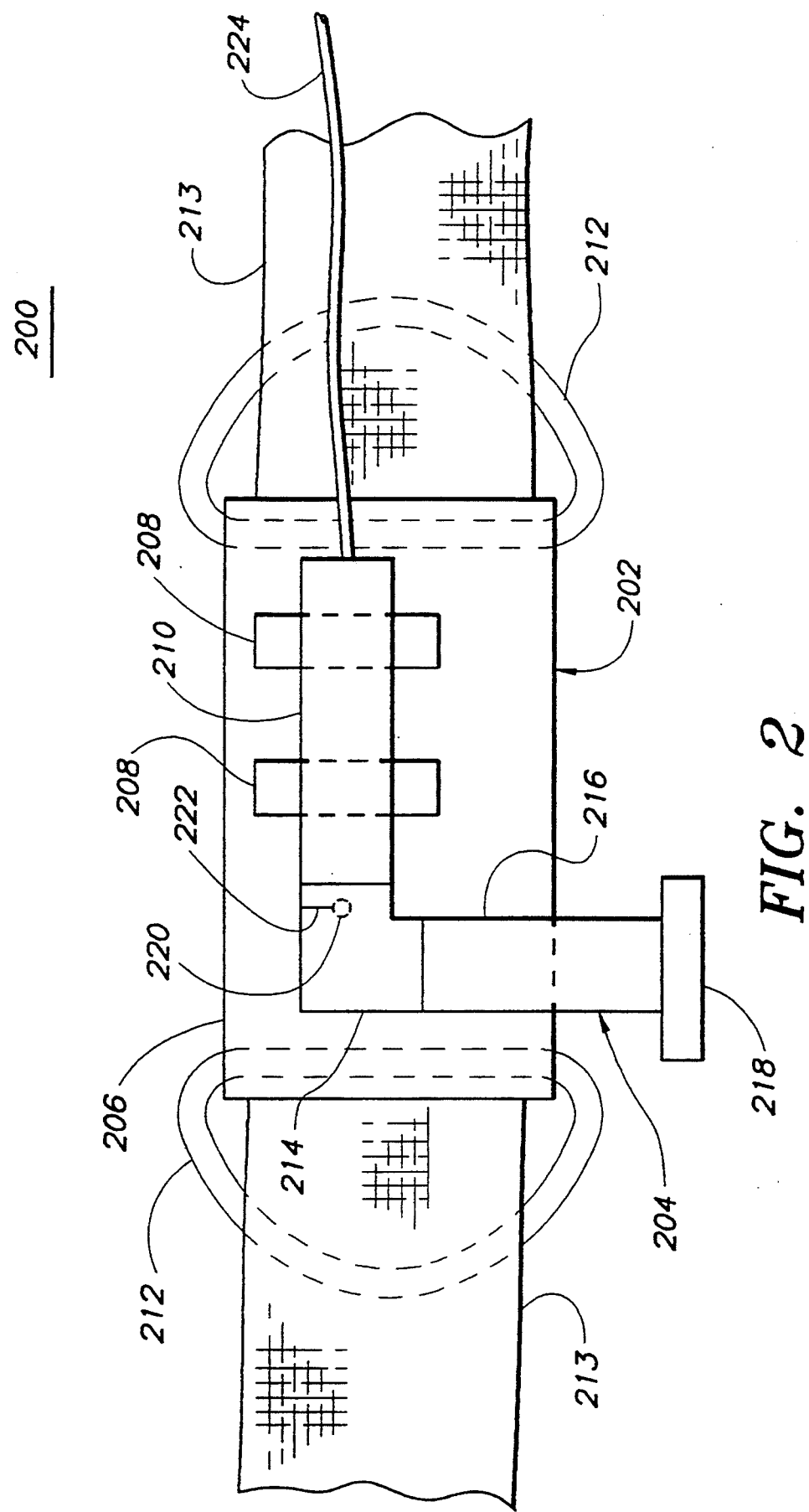
FIG. 2 is a front view of the sensor module of the apparatus of FIG. 1.

Referring now to FIG. 2, there is shown a front view of sensor module 200 of apparatus 100 according to a preferred embodiment of the present invention. Sensor module 200 comprises fixed portion 202 and movable portion 204. Fixed portion 202 further comprises back plate 206, mounting clamps 208, pipe 210, and "D" rings 212. Movable portion 204 comprises elbow 214, pipe 216, and housing 218.

In a preferred embodiment, back plate 206 of fixed portion 202 is a 2-inch by 3-inch piece of flexible, heat-formable plastic manufactured by Aquaplast Co. which provides a mounting surface for sensor module 200. Pipe 210 is a three-inch piece of one-half-inch polyvinylchloride (PVC) pipe and mounting clamps 208 are two one-half-inch PVC mounting straps. Pipe 210 is rigidly connected to back plate 206 by mounting clamps 208. Fixed portion 202 may be assembled by screwing back plate 206 through mounting clamps 208 and into pipe 210 from the rear of back plate 206. Tapped screw hole 220 is drilled into pipe 210 near one end.

Two "D" rings 212 are connected to back plate 206. Each "D" ring 212 may be joined to back plate 206 by heating back plate 206 and wrapping an end of the heat-softened back plate 206 through the "D" ring 212 and pulling the end back around to adhere to back plate 206, thereby forming a loop of plastic with one side of the "D" ring passing through the loop. Straps (not shown) may then be looped through "D" rings 212 to secure sensor module 200 to the user's torso or other body part, as desired. In a preferred embodiment, the straps have Velcro fastening devices to provide flexibility in securing sensor module 200 to the user's body.

Housing 218 of movable portion 204 houses the mercury switch (not shown) that senses when the attitude of the user's back or other body part exceeds a specific attitude range. The mercury switch is preferably mounted within housing 218 with the longitudinal (i.e. long) axis of the mercury switch perpendicular to the page in FIG. 2. Housing 218 is rigidly mounted to pipe 216, a three-inch piece of one-half-inch PVC pipe. Pipe 216 is also rigidly mounted to elbow 214, a one-half-inch PVC elbow coupling. Elbow 214 contains slot 222.

A screw (not shown) runs through slot 222 of elbow 214 and into hole 220 of pipe 210. When the screw is loose, movable portion 204 may be rotated relative to fixed portion 202. The screw may be tightened to fix the angle of rotation between movable portion 204 and fixed portion 202. This ability to adjust the orientation between movable portion 204 and fixed portion 202 allows the user to adjust the sensitivity of sensor module 200 by altering the attitude range for the mercury switch.

Those skilled in the art will understand that a mercury switch can be used to detect when the attitude crosses a specific threshold angle along a specific axis of rotation. When the attitude is on one side of the threshold angle, the mercury switch is open or disengaged, and when the attitude is on the other side of the threshold angle, the mercury switch is closed or engaged. A transition within the mercury switch from open to closed or from closed to open indicates that the attitude has crossed the threshold angle.

A specific attitude range is defined, for example, as the set of angles for which the mercury switch is disengaged. By controlling the relative orientation between mercury switch 108 and the user's back, apparatus 100 can be used to define a range of acceptable attitudes for the user's back, e.g., those angle within 20 degrees of "perfect" posture.

Electrical power between the mercury switch of sensor module 200 and the controller module of apparatus 100 is provided by cable 224. Cable 224 is a flexible, expandable cable that runs from the mercury switch in housing 218 through pipe 216, elbow 214, and out pipe 210 to the controller module.

Figure 4:
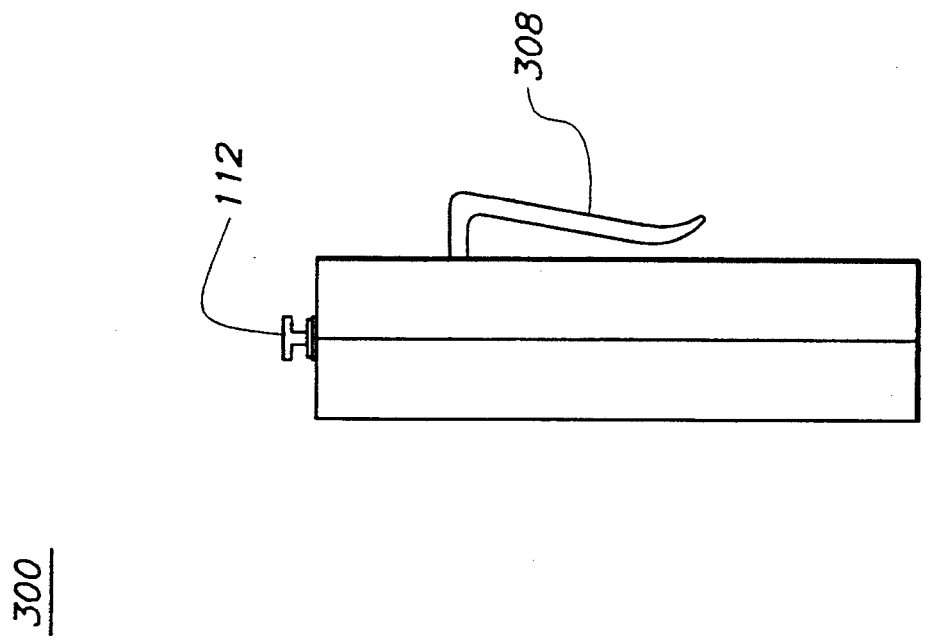
FIGS. 3 and 4 are a front view and a side view, respectively, of the controller module of the apparatus of FIG. 1.
Figure 3:
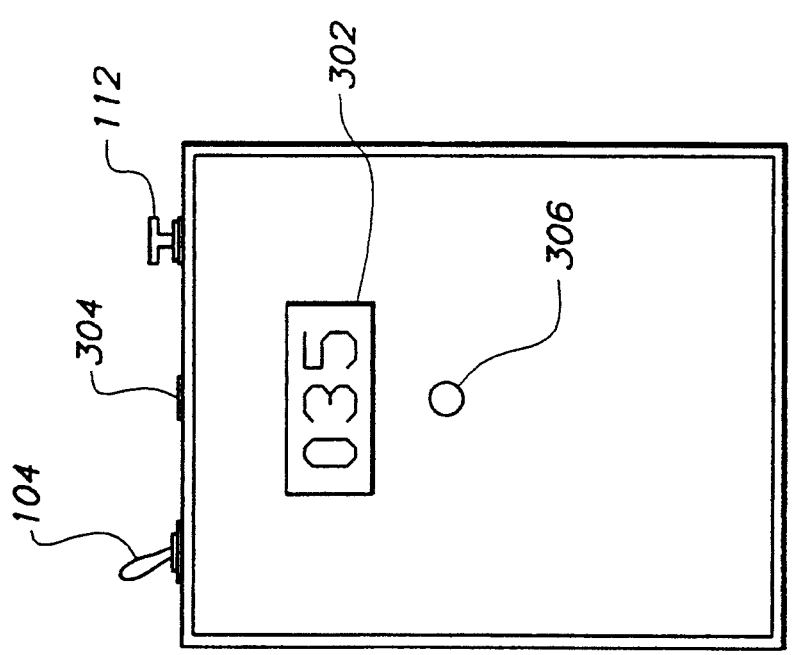

Referring now to FIGS. 3 and 4, there are shown a front view and a side view, respectively, of controller module 300 of apparatus 100 according to a preferred embodiment of the present invention. FIG. 3 shows power switch 104 and reset switch 12 of FIG. 1. In a preferred embodiment, display 302 is a light emitting diode (LED) device that displays the current counter value. Input jack 304 receives an end of cable 224 of FIG. 2 to provide the electrical connection between controller module 300 of FIG. 3 and sensor module 200 of FIG. 2. Hole 306 provides a conduit for the audible tone from electronic buzzer 106 of FIG. 1, which is housed within controller module 300. FIG. 4 shows reset switch 112 of FIG. 1 and clip 308 which may be used to secure controller module 300 to the user's body, for example, by clipping controller module 300 to the strap used to secure sensor module 200 to the user's torso or to the user's shirt pocket or pant waistline. In a preferred embodiment, controller module 300 has dimensions of approximately three and one-half inches wide by five and one-half inches long by one and one-quarter inches deep.

Further Description of Electrical Circuitry

Figure 5:
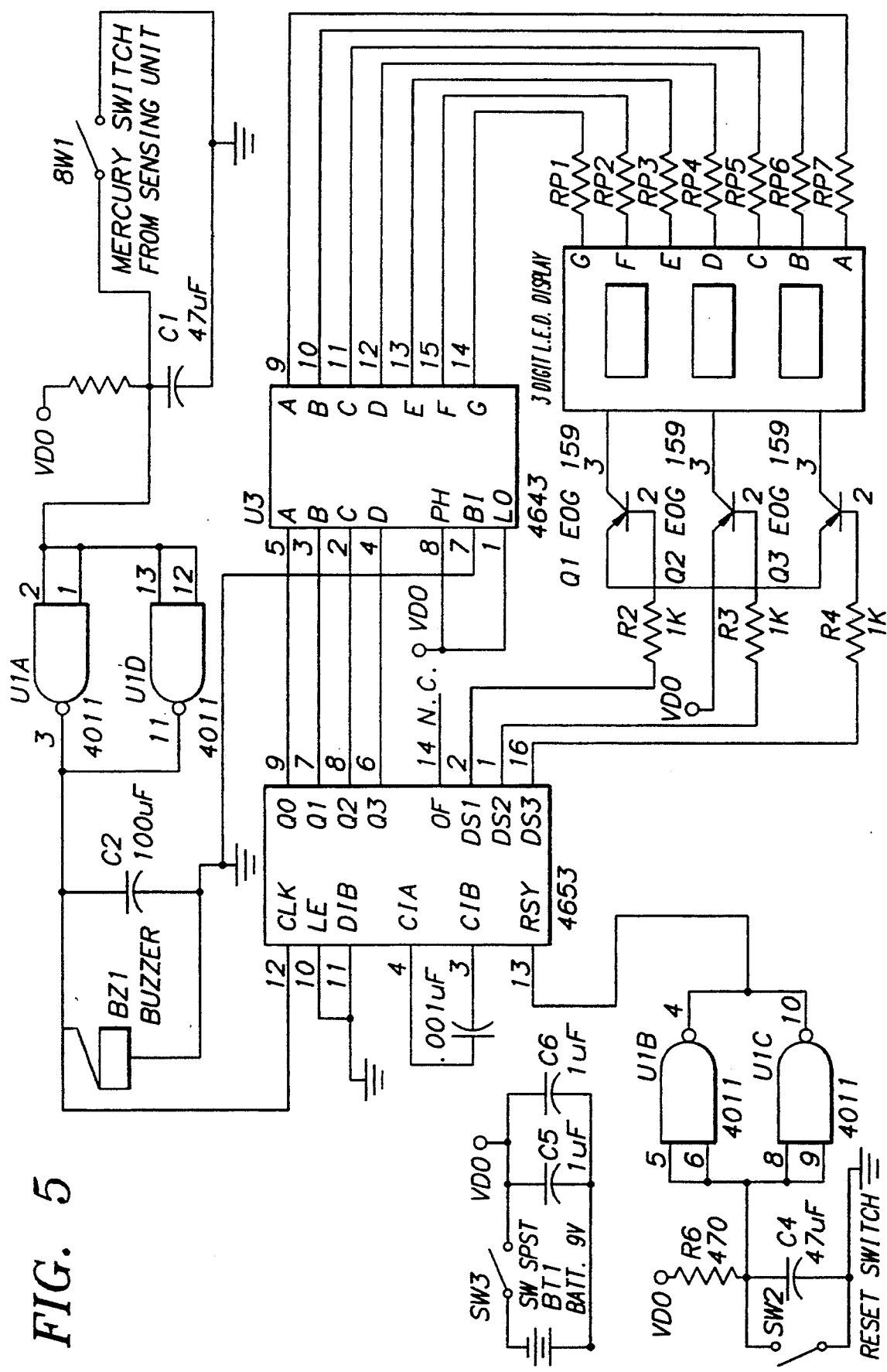
FIG. 5 is a schematic diagram of the electrical circuitry of the apparatus of FIG. 1.

Referring now to FIG. 5, there is shown a schematic diagram of the electrical circuitry of a preferred embodiment of apparatus 100. Battery BT1 provides electrical power to apparatus 100 as voltage VDD, where voltage VDD may range between +3 the +15 volts. Battery BT1 is preferably a commercial 9-volt transistor battery. When single-pole, single-throw power switch SW3 is placed in the "ON" position, voltage VDD is supplied to the circuitry of apparatus 100.

Voltage VDD is supplied through 470-ohm resistor R5 to pins 5, 6, 8, and 9 of combined NAND gates U1B and U1C making these pins high with respect to ground. Gates U1B and U1C are two of the four gates of quad NAND gate U1, a CMOS CD 4011 integrated circuit. (NAND gates U1A and U1D are the other two gates of quad gate U1.) The high state on pins 5, 6, 8, and 9 causes the outputs of gates U1B and U1C (pins 4 and 10, respectively) to go to a low state.

When reset switch SW2 is engaged, it shorts 47-microfarad capacitor C4 to ground and causes pins 5, 6, 8, and 9 of gates U1B and U1C to go to a low state. This then drives the outputs of gates U1B and U1C (pins 4 and 10, respectively) to a high state and supplies this high state to pin 13 of counter U2 which then resets the counter value to zero. Capacitor C4 is used to debounce the reset switch (i.e., to ensure that the outputs of gates U1B and U1C go to a high state only once with each single push of reset switch SW2). Reset switch SW2 is preferably a normally-open single-pole single-throw minimomentary push-button switch.

Voltage VDD is also supplied through 470-ohm resistor R1 to pins 1, 2, 12, and 13 of combined NAND gates U1A and U1D, making these pins high with respect to ground. In this state, the outputs of gates U1A and U1D (pins 3 and 11, respectively) are at a low state and buzzer BZ1 will not sound. Gates U1A and U1D are combined to provide increased drive current to buzzer BZ1 and the rest of the electrical circuitry.

When the attitude of the back of the user of apparatus 100 exceeds the specific attitude range, mercury switch SW1 within sensor module 200 of FIG. 2 will engage. When mercury switch SW1 is engaged, it shorts capacitor C1 and makes pins 1, 2, 12, and 13 of gates U1A and U1D go to a low state. This causes the outputs of gates U1A and U1D (pins 3 and 11, respectively) to be high with respect to ground and enables buzzer BZ1 to emit a tone indicating that the specific attitude range has been exceeded (i.e., that an attitude violation has occurred). Mercury switch SW1 is preferably a single-pole double-throw mercury switch. Buzzer BZ1 is preferably a piezoelectronic buzzer with built-in driver. Forty-seven-microfarad capacitor C1 is utilized in combination with 100-microfarad capacitor C2 to debounce mercury switch SW1 when it is activated.

When the attitude of the user's back returns to within the specific attitude range, mercury switch SW1 is disengaged and pins 1, 2, 12, and 13 of gates U1A and U1D return to a high state. This causes the outputs of gates U1A and U1D (pins 3 and 11, respectively) to return to a low state and disables buzzer BZ1.

The transition of the outputs of gates U1A and (pins 3 and 11, respectively) from a high state to a low state (when mercury switch SW1 disengages) increments clock input pin 12 of counter U2. Counter U2 is preferably a CMOS 4553 integrated circuit, a three-digit binary-coded decimal (BCD) counter. Counter U2 is incremented one time for every violation of the specific attitude range.

Each time pin 12 of counter U2 receives a clock pulse that corresponds to a transition from a high state to a low state, counter U2 increments its internal counter value by one. Counter U2 then transmits the three BCD digits that correspond to the counter value to BCD-to-decimal converter U3, a CMOS 4543 integrated circuit.

Counter U2 transmits the counter value to converter U3 one BCD digit at a time by way of pins 9, 7, 6, and 5 of counter U2. The rate at which the BCD digits of the counter value are transmitted is controlled by an internal digit-select oscillator built into counter U2. 0.001-microfarad capacitor C3 is an external component of the digit-select oscillator and is connected to pins 3 and 4 of counter U2.

Pins 10 and 11 (latch enable and disable, respectively) of counter U2 are disabled by tying them to ground. Pin 14 of counter U2 is not connected.

The BCD outputs of counter U2 (pins 9, 7, 6, and 5) are connected to inputs A, B, C, and D of converter U3 (pins 5, 3, 2, and 4, respectively). Converter U3 converts each received BCD value into a seven-segment decimal number that is output on pins 9, 10, 11, 12, 13, 15, and 14 of converter U3 (outputs A, B, C, D, E, F, and G, respectively). Each of these output lines corresponds to a light emitting diode (LED) in three-digit seven-segment multiplexed common-anode LED display K-43. One-kilo-ohm resistors RP1 through RP7 are used to limit current to LED display K-43, where the seven resistors are preferably part of an eight-resistor resistor pack, the eighth resistor being unused.

Outputs A, B, C, D, E, F, and G of converter U3 are connected to inputs A, B, C, D, E, F, and G of LED display K-43 with resistors RP1, RP2, RP3, RP4, RP5, RP6, and RP7 in line with each output, respectively. The rate at which the seven-segment decimal numbers are transmitted from converter U3 to LED display K-43 is controlled by the internal digit-select oscillator of counter U2. Pins 6 and 1 of converter U3 are tied to voltage VDD. Pin 7 of converter U3 is tied to ground.

Each of PNP transistors Q1, Q2, and Q3 has its collector 3 tied to an anode corresponding to a different digit of three-digit LED display K-43. Transistors Q1, Q2, and Q3 correspond to digits #1, #2, and #3 of display K-43, respectively, where digit #1 is the least significant digit and digit #3 is the most significant digit. The emitter 1 of each transistor is connected to voltage VDD. The base 2 of each transistor is connected to a corresponding digit-select output from counter U2 through a biasing resistor (i.e., pins 2, 1, and 15 of counter U2 to transistors Q1, Q2, and Q3 through one-kilo-ohm resistors R2, R3, and R4, respectively). Transistors Q1, Q2, and Q3 are preferably ECG 159 transistors, distributed by Philips ECG of Williamsport, Pa., or their equivalent.

Each time the internal digit-select oscillator of counter U2 increments by one, it puts a low state on one of the three digit-select outputs of counter U2 (DS1, DS2, or DS3). This low state goes through the biasing resistor to the base 2 of the corresponding transistor turning that transistor on, thereby supplying voltage VDD to the anode of the corresponding digit of LED display K-43 to turn that digit display on. At the same time, counter U2 transmits the BCD value of that digit to converter U3, which converts the BCD value to a seven-segment output and transmits the seven-segment output to LED display K-43.

For example, if the BCD counter value is equivalent to the decimal value "638," counter U2 would first command digit #1 (the least significant digit) of LED display K-43 to turn on and display the digit "8." Counter U2 would then command digit #2 of LED display K-43 to turn on and display the digit "3." Counter U2 would then command digit #3 (the most significant digit) of LED display K-43 to turn on and display the digit "6." Counter U2 repeats this sequence at a rate high enough so that the naked eye cannot "see" that only one of the three digits is being displayed at a given time.

One-microfarad capacitor C5 and 0.1-microfarad capacitor C6 are used to stabilize the power supply of battery BT1. Although not explicitly shown in FIG. 5, voltage VDD is also supplied to gate U1 at pin 14, to counter U2 at pin 16, and to converter U3 at pin 16. Similarly, ground is supplied to gate U1 at pin 7, to counter U2 at pin 8, and to converter U3 at pin 8.

Those skilled in the art will understand that, in alternative preferred embodiments, three single-digit LED displays may be used in place of three-digit LED display K-43 by tying the corresponding inputs (A, B, C, D, E, F, and G) of each of the single-digit displays together. In addition, a liquid crystal display (LCD) device may be used in place of LED display K-43. Furthermore, the electrical circuitry of apparatus 100 may be reconfigured for common-cathode displays in place of common-anode display K-43. Similarly, piezo buzzer BZ1 may be replaced by any appropriate buzzer or speaker with an internal driver circuit or a light, if desired.

Those skilled in the art will also understand that the electrical circuitry of apparatus 100 (with the exception of mercury switch SW1 and reset switch SW2) may be replaced by an electronic counting module, such as a CUB III module manufactured by Red Lion Controls and distributed by Digi-Key Corporation of Thief River Falls, Minn. 56701-0677. It will also be understood that mercury switch SW1 may be replaced by any suitable sensor that detects changes in attitude.

It will be further understood by those skilled in the art that apparatus 100 may be used to monitor the attitude of the parts of the user's body other than the back. For example, apparatus 100 may be strapped to the user's head to monitor the number of times the user leans his head too far to the left or right. Moreover, an apparatus within the scope of the present invention could be designed with more than one mercury switch to monitor body attitude along more than one axis. For example, an apparatus within the scope of the present invention having two mercury switches aligned at right angles could be used to monitor the attitude of the user's head along two degrees of freedom where the head can tilt either side-to-side or front-to-back.

As described earlier in this specification in conjunction with FIG. 1, in a preferred embodiment, apparatus 100 comprises two separate modules—a sensor module and a controller module—that are connected by a cable. Those skilled in the art will understand that apparatuses within the scope of the present invention may comprise a single module that contains all of the elements of apparatus 100 depicted in FIG. 1.

It will be further understood that apparatuses within the scope of the present invention may comprise separate sensor and controller modules that are not connected by a cable. For example, the sensor module may comprise a separate power supply and a radio transmitter that emits a radio-frequency signal when an attitude violation occurs. The controller module may then comprise a radio receiver to receive and process the signal from the sensor module to sound the buzzer and increment the counter.

It will be further understood that various changes in the details, materials, and arrangements of the parts which have been described and illustrated in order to explain the nature of this invention may be made by those skilled in the art without departing from the principle and scope of the invention as expressed in the following claims.

What is claimed is:

1. An apparatus for attachment to a body part of a user, comprising:
   (a) a sensor module comprising:
      (1) sensing means for generating a first signal when the attitude of said body part, relative to the direction of the force of gravity, falls outside an attitude range;
      (2) a first section; and
      (3) a second section for housing said sensing means, wherein said first section is releasably secured to said body part and said second section is releasably coupled to said first section at one of two or more orientations to adjust said attitude range;
   (b) a controller module comprising:
      (1) a power supply for providing electrical power to said sensor module and said controller module;
      (2) counting means for receiving said first signal and for incrementing a counter value after receiving said first signal; and
   (c) means for electrically connecting said sensor module to said controller module to transfer power from said power supply to said sensing means and to transmit said first signal from said sensing means to said counting means;
   wherein said second section comprises a first cylindrical portion, said first section comprises a second cylindrical portion, one end of said first cylindrical portion fitting over one end of said second cylindrical portion, and said sensor module further comprises fastening means for releasably coupling said second section to said first section at said one of said two or more orientations.

2. The apparatus of claim 1, wherein said controller module further comprises a buzzer for receiving said first signal from said sensing means and for generating an audible tone in response to receiving said first signal.

3. The apparatus of claim 1, wherein said sensing means is a mercury switch.

4. The apparatus of claim 1, wherein said counting means is a binary-coded decimal counter and said controller module further comprises a binary-coded decimal to decimal converter and a light emitting diode display, wherein said counter generates a binary-coded decimal signal in accordance with said counter value, said converter receives said binary-coded decimal signal from said counter and converts said binary-coded decimal signal to a converted signal, and said display receives said converted signal from said converter and displays a decimal number in accordance with said converted signal.

5. The apparatus of claim 4, wherein said counter is a CMOS 4553 integrated circuit, said converter is a CMOS 4543 integrated circuit, and said display is a three-digit multiplexed display, wherein said counter transmits one binary-coded digit of said counter value to said converter at a time, said converter transmits one digit of said converted counter value to said display at a time, and said display displays one digit of said decimal number at a time.

6. The apparatus of claim 1, wherein said controller module further comprises a reset switch, wherein said reset switch causes said counting means to reset said counter value to zero when said reset switch is engaged.

7. An apparatus for attachment to a body part of a user, comprising:
   (a) a sensor module comprising:
      (1) sensing means for generating a first signal when the attitude of said body part, relative to the direction of the force of gravity, falls outside an attitude range;
      (2) a first section; and
      (3) a second section for housing said sensing means, wherein said first section is releasably secured to said body part and said second section is releasably coupled to said first section at one of two or more orientations to adjust said attitude range;
   (b) a controller module comprising:
      (1) a power supply for providing electrical power to said sensor module and said controller module;
      (2) counting means for receiving said first signal and for incrementing a counter value after receiving said first signal; and
   (c) means for electrically connecting said sensor module to said controller module to transfer power from said power supply to said sensing means and to transmit said first signal from said sensing means to said counting means;
   wherein said counting means is a binary-coded decimal counter and said controller module further comprises a binary-coded decimal to decimal converter and a light emitting diode display, wherein said counter generates a binary-coded decimal signal in accordance with said counter value, said converter receives said binary-coded decimal signal from said counter and converts said binary-coded decimal signal to a converted signal, and said display receives said converted signal from said converter and displays a decimal number in accordance with said converted signal.

8. The apparatus of claim 7, wherein said controller module further comprises a buzzer for receiving said first signal from said sensing means and for generating an audible tone in response to receiving said first signal.

9. The apparatus of claim 7, wherein said sensing means is a mercury switch.

10. The apparatus of claim 7, wherein said counter is a CMOS 4553 integrated circuit, said converter is a CMOS 4543 integrated circuit, and said display is a three-digit multiplexed display, wherein said counter transmits one binary-coded digit of said counter value to said converter at a time, said converter transmits one digit of said converted counter value to said display at a time, and said display displays one digit of said decimal number at a time.

11. The apparatus of claim 7, wherein said controller module further comprises a reset switch, wherein said reset switch causes said counting means to reset said counter value to zero when said reset switch is engaged.

* * * * *